United States Patent

Hosoi et al.

[11] Patent Number: 5,956,121
[45] Date of Patent: Sep. 21, 1999

[54] TELECOMMUNICATION SYSTEM FOR EXAMINING AN EYE AND AN OPHTHALMIC APPARATUS USED FOR THE SYSTEM

[75] Inventors: Yoshinobu Hosoi, Gamagori; Hirohisa Terabe, Toyokawa; Toshiro Kobayashi, Anzyo, all of Japan

[73] Assignee: Nidek Co., Ltd., Japan

[21] Appl. No.: 09/021,122

[22] Filed: Feb. 10, 1998

[30] Foreign Application Priority Data

Feb. 10, 1997 [JP] Japan ..................................... 9-041482

[51] Int. Cl.⁶ ...................................................... A61B 3/10
[52] U.S. Cl. .......................................................... 351/205
[58] Field of Search ..................................... 351/200, 205, 351/206; 600/301; 128/904, 905, 906, 920

[56] References Cited

U.S. PATENT DOCUMENTS

| | | | |
|---|---|---|---|
| 5,444,504 | 8/1995 | Kobayashi et al. ..................... | 351/237 |
| 5,610,671 | 3/1997 | Hosoi et al. ............................. | 351/200 |
| 5,627,612 | 5/1997 | Hayashi .................................. | 351/200 |
| 5,701,904 | 12/1997 | Simmons et al. ....................... | 600/301 |

FOREIGN PATENT DOCUMENTS 10-14881  1/1998  Japan .

Primary Examiner—George Manuel
Attorney, Agent, or Firm—Finnegan, Henderson, Farabow, Garrett & Dunner, L.L.P.

[57] ABSTRACT

A communication system for examining an eye comprising plural eye examining units which include testing device for testing visual performance of an eye to be examined and operating device for operating the testing device, each of said units is connected through a communication network, and each of said eye examining units comprising sending device for sending the data obtained by the testing device to another eye examining unit, receiving device for receiving the data sent from another eye examining unit, and instruction device for giving instructions to the testing device of another eye examining unit.

14 Claims, 5 Drawing Sheets

TELECOMMUNICATION SYSTEM FOR EXAMINING AN EYE AND AN OPHTHALMIC APPARATUS USED FOR THE SYSTEM

BACKGROUND OF THE INVENTION

1. Field of the Invention

The present invention relates to a telecommunication system for examining an eye, and more particularly to the telecommunication system for examining an eye by remotely controlling an ophthalmic apparatus which examines visual performance.

2. Description of Related Art

Currently, a visual acuity test of an eye to be examined or a subjective examination to prescribe a spectacle lens requires a presence of an examiner at the same location as the examinee and each ophthalmic apparatus is directly operated by the examiner.

However, in the process of a subjective examination or the like, to prescribe a spectacle lens, different results are easily obtained depending on the examiner's experience in, or knowledge of, optometry and, therefore, the accuracy in an examination is largely influenced by the examiner's experience in, or knowledge of, optometry. An examiner with little experience in optometry may not be able to carry out an examination sufficiently depending on a state of refractive power of the eye. In addition, at an optician's shop, an eye clinic or the like, an examination can not be performed without a presence of an examiner.

Therefore, there is a problem that each optician's shop, an eye clinic or the like should give training to bring up an examiner with necessary experience in, and knowledge of, optometry and station him.

SUMMARY OF THE INVENTION

The present invention has been made in view of the above circumstances and has an object to overcome the above problems and to provide a telecommunication system, with which an examiner is able to operate an ophthalmic apparatus and perform an ophthalmic examination without being present with an examinee.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a telecommunication system for examining an eye comprises plural eye examining units which include testing means for testing visual performance of an eye to be examined and operating means for operating the testing means, each of the units is connected via a communication network, and each of the eye examining units comprising, sending means for sending the data obtained by the testing means to another eye examining unit, receiving means for receiving the data sent from another eye examining unit, instruction means for giving instructions to the testing means of another eye examining unit.

In another aspect of the present invention, an ophthalmic apparatus used for a telecommunication system comprises testing means for testing visual performance of an eye to be examined, operating means for activating the testing means, which is placed at a separate location than an examinee, telecommunication means for connecting the operating means and the testing means via a communication network, communication means to enable communication between an examiner operating the operating means and the examinee being examined with the testing means.

Further, in another aspect of the invention, the ophthalmic apparatus comprises testing means for testing visual performance of an eye to be examined, a first operating means for activating the testing means, which is placed at the same location as an examinee, a second operating means for activating said testing means, which is placed at a separate location than the examinee, telecommunication means for connecting the second operating means and the testing means via a communication network, and communication means to enable communication between an examiner operating the second operating means and the examinee being examined with the testing means via the communication network.

According to the present invention, a remote operation of an examination apparatus may be realized by a skilled examiner at a separate location than, or a remote location from, an examinee, therefore the amount of work in current examination procedures can be reduced.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of one preferred embodiment of a telecommunication system for examining an eye and an ophthalmic apparatus used for the system embodying the present invention will be given referring to the accompanying drawings.

Figure 1:
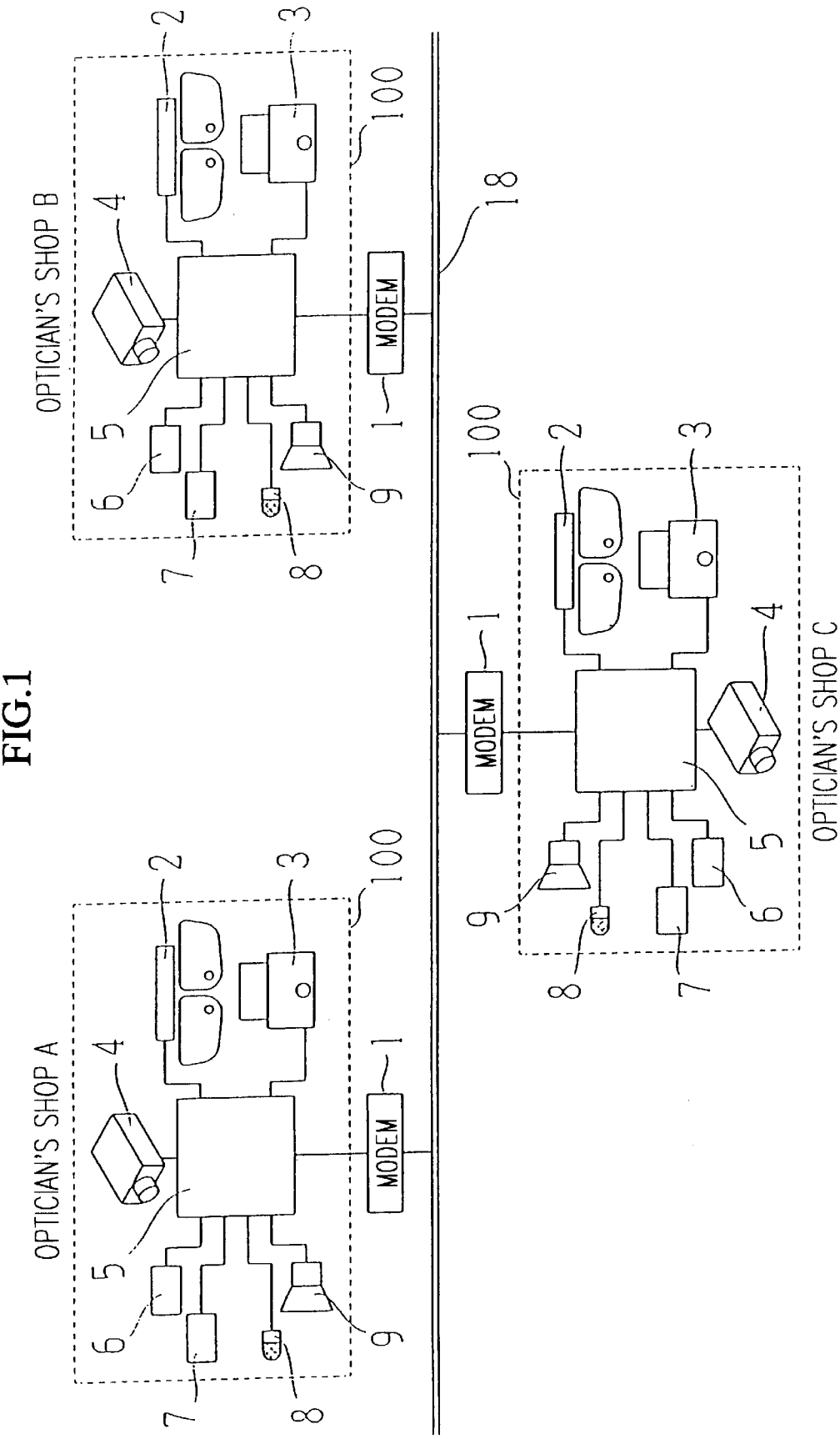
FIG. 1 is an overview showing a whole schematic configuration of a telecommunication system for examining an eye of the present invention.

In FIG. 1, there is shown the overview of a whole schematic configuration of the telecommunication system for examining an eye according to the present invention.

Numeral 100 each indicates an eye examining unit placed at each optician's shop and the eye examining units 100s are connected to a public communication network 18, such as a telephone network or the like via a modem 1, therefore, variety signals can be mutually send and received. The eye examining unit 100 includes a subjective refractive power measuring device 2, a controller 3, a target (chart) presenting device 4, a relay unit 5, an objective refractive power measuring device 6, a lens meter 7, a microphone 8 and a speaker 9.

Figure 2:
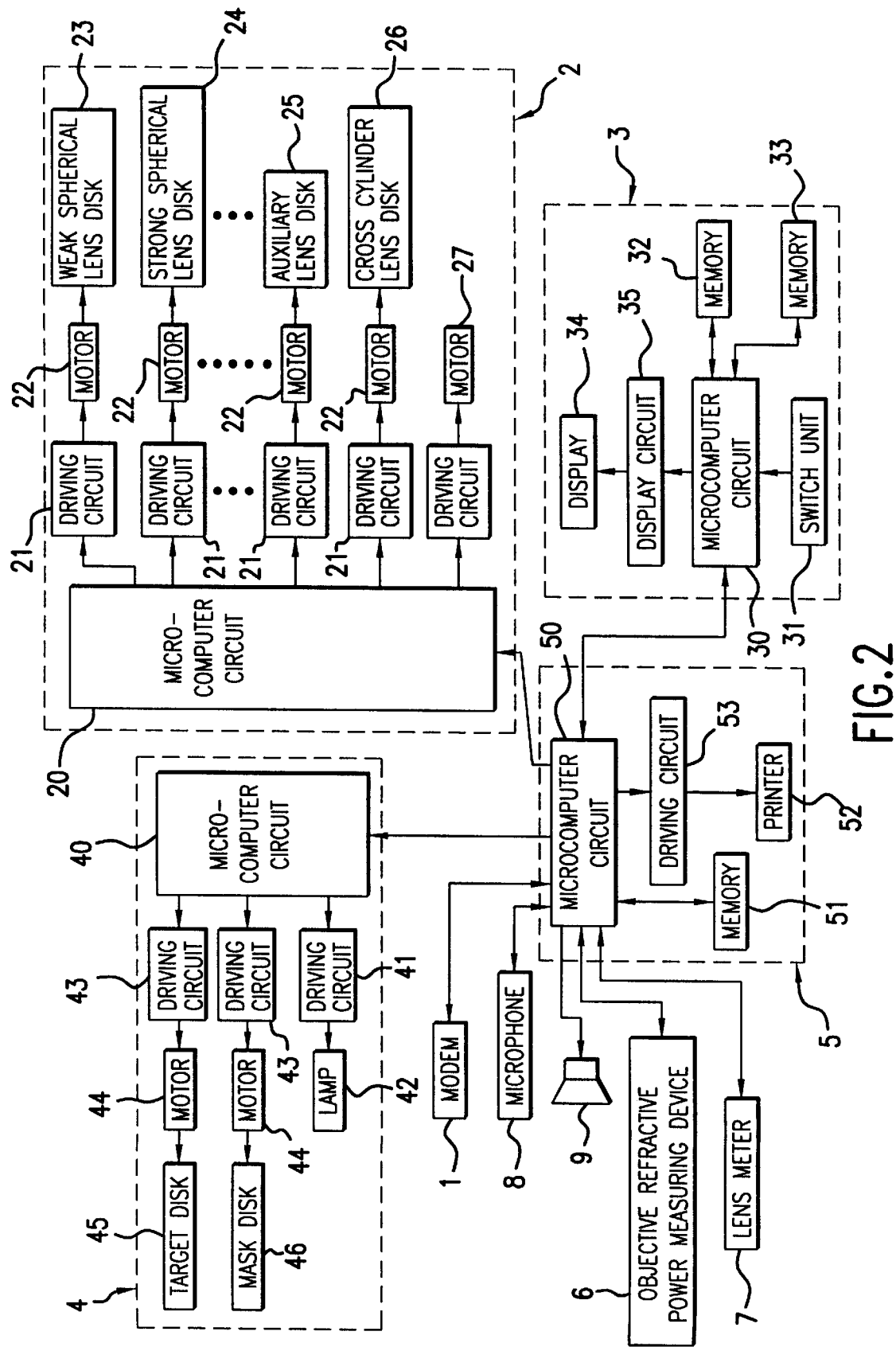
FIG. 2 is a block diagram showing each component of an eye examining unit shown in FIG. 1.

Each component of the eye examining unit 100 will be described with reference to the FIG. 2, a block diagram. The subjective refractive power measuring device 2 includes a binocular lens unit for arranging optical elements having various optical characteristics in their corresponding test windows by switching electrically, a suspending section to suspend the binocular lens unit and the like. Based on the conditions such as a distance between pupils of the eyes or the like, the lens unit is driven by a motor 27 installed in the suspending section, so that the eyes may be positioned in front of the test windows. Installed in the lens unit is a lens disk provided with various optical elements such as a weak spherical lens disk 23, a strong spherical lens disk 24, an auxiliary lens disk 25, a cross cylinder lens disk 26, and the like. The microcomputer circuit 20 rotates the lens disk by driving the motor 22 though the driving circuit 21 based on the inputted command signal, so as to arrange optical systems for giving refractive power to the eye in their corresponding test windows.

The controller 3 includes a microcomputer circuit 30, a switch unit 31 for inputting a control command, a memory 32 for storing a control program such as a program for examining an eye and the like, a memory 33 for storing test data and the like, a display 34 for displaying various optometry information thereon for the examiner, and a display circuit 35 of the display 34 and the like.

The target (chart) presenting device 4 is a device for presenting various test targets (charts) to an examinee. When the command signal is inputted to a microcomputer circuit 40 from a relay unit 5, the microcomputer circuit 40 turns on a lamp 42 via a driving circuit 41, drives a motor 44 via a driving circuit 43 and rotates a target (chart) disk 45 on which targets (charts) for a visual acuity test is illustrated, and a mask disk 46, thereby a test target (chart) is projected on an unillustrated screen placed in front of the eye.

The relay unit 5 performs relay of the telecommunication among each device. The relay unit 5 includes a microcomputer circuit 50, a memory 51 for storing measurement data, a printer 52 for outputting a result of measurement, a driving circuit 53 for driving the printer 52 and the like.

The objective refractive power measuring device 6 projects a target for measurement onto the fundus of the eye and measures a refractive power of the eye based on a detection signal obtained by detecting projected-target image of the fundus using photo-detector. The lens meter 7 is utilized for measuring lens power of the previous spectacles, or the like, of the examinee. The data measured by the objective refractive power measuring device 6 and the lens meter 7 is stored into the memory 51 in the relay unit 5 and the data can be fetched and used when necessary.

The microphone 8 and the speaker 9 are utilized for performing conversations and communications for questions and answers between the examinee and the examiner at the separate locations.

Figure 3:
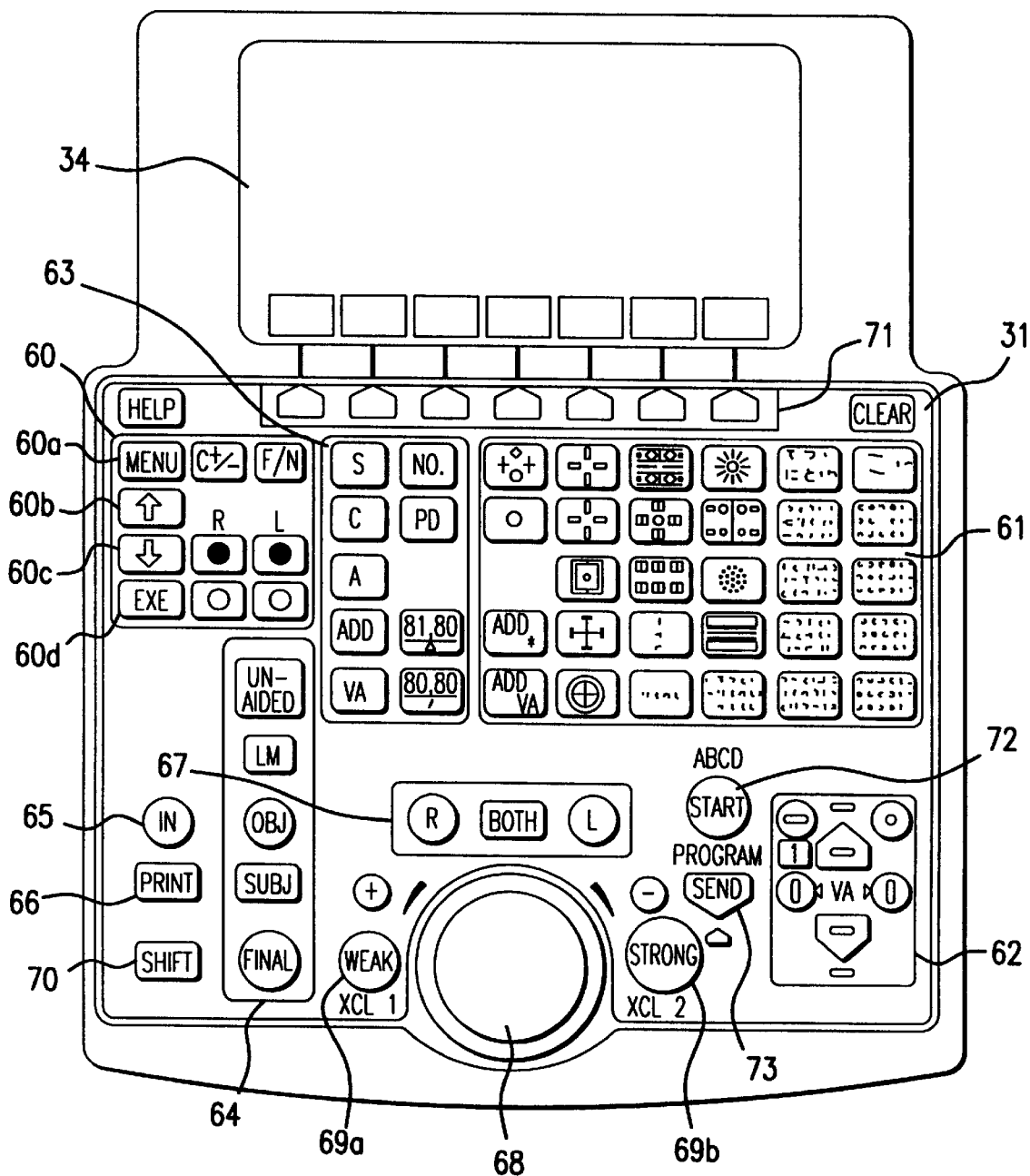
FIG. 3 is a top view showing a controller of the examining unit.

FIG. 3 is a top view showing the controller 3. The switch unit 31, shown in the FIG. 3, is provided with various switches 60 is a setting changeover switch group having switches used for switching a display screen of the display 34 to a menu screen for parameter setting and the like. 61 is a target (chart) switch group for changing a test target (chart), which is made to be presented by the target (chart) presenting device 4, 62 is a mask switch group to put a necessary mask on a test target (chart) to be presented, 63 is a change mode designation switch group for designating a mode to modify the measurement data and the like, 64 is an input data designation switch group for designating a mode to input or measure data, 65 is a data input switch used for inputting data transmitted from the objective refractive power measuring device 6, the lens meter 7 and the like, 66 is a print switch, 67 is a switch for designating an eye to be measured, and 68 is a dial switch used for modifying measured data and for inputting numerical values. 69a and 69b are switches for changing over cross cylinders, which are also used for adjusting the condition of visibility at the prescription stage. 70 is a shift switch by which switch functions are added by depressing this switch with other switches. 71 is a function switch group used for selecting switches corresponding to information displayed in predetermined position below the screen of the display 34. Further, 72 is a start switch for executing optometry in accordance with a program, and 73 is a switch for proceeding the examination stage in optometry by the program to the next one.

With the eye examining unit 100 having the above-described construction, an ophthalmic examination is performed at an optician's shop by operating the controller 3. Other eye examining units 100s placed at other optician's shops basically have the same construction.

Hereinafter, operations of the telecommunication system of the preferred embodiment will be described. In this embodiment, an examiner operates the eye examining unit 100B, placed at the optician's shop B and an examinee is examined by the eye examining unit 100, placed at the optician's shop A. Hereinafter, to differentiate those eye examining units 100s placed at the optician's shop A and B, the letter B will appear with each component of the eye examining unit at the optician's shop B.

Figures 4, 5:
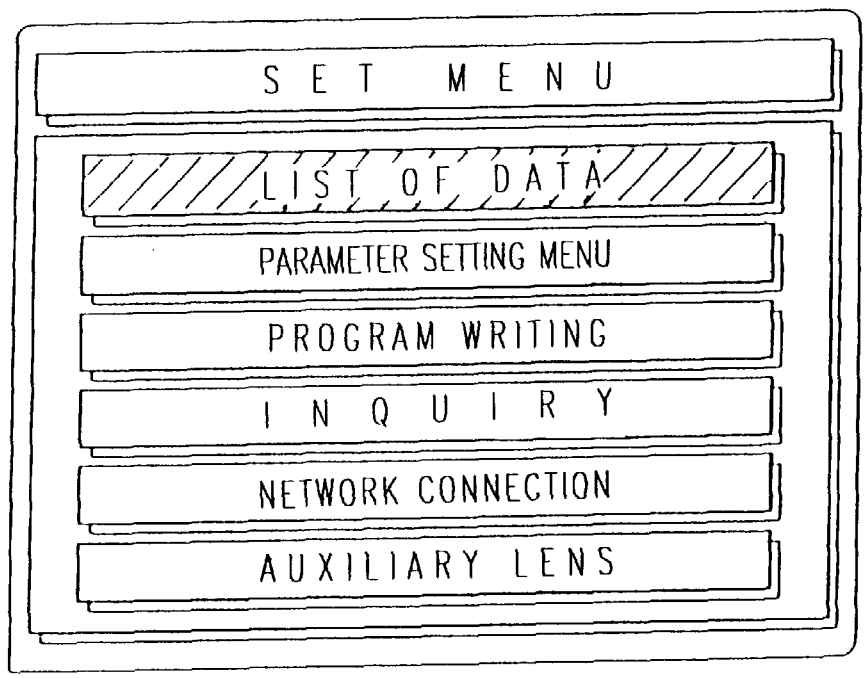
FIG. 4 is a view showing an example of a set menu displayed on a screen of the examining unit.
FIG. 5 is a view showing an example of a screen for an examination displayed on a screen.

Prior to the examination, an assistant at the optician's shop A goes through the necessary preparation. The assistant measures the objective refractive power of an eye of an examinee by using the objective refractive power measuring device 6. If the examinee wears spectacles, the assistant measures the degree of the spectacles by using the lens meter 7. The measured data of the objective refractive power of the eye and the measured data of the previous spectacles are to be stored in the memory 33 on the side of the controller 3 via the relay unit 5, responding to an operation of the switches on the controller 3 by the assistant. The assistant also inputs inquiry information of the examinee. By depressing the menu switch 60a of the controller 3, a set menu screen, as shown in FIG. 4, is displayed on a screen of the display 34, therefore, the reverse part is made to be shifted to /inquiry/ using movement switches 60a and 60b, and the menu is selected by using an execution switch 60d. Then the screen shown on the display 34 is switched to a screen for inputting inquiry information, so that information of the examinee, which is necessary for performing ophthalmic examination including the age and the purpose of taking the ophthalmic examination and so on, can be inputted. The assistant positions the test windows of the subjective refractive power measuring device 2 in front of the examinee's eyes (or the subjective refractive power measuring device 2 may be prepared at the later examination stage, when the device is actually needed) and sets the target (chart) presenting device 4, the microphone 8 and the speaker 9 to complete the preparation for an examination.

After the preparation for the examination is made, the assistant connects the eye examining unit with the eye examining unit 100B on the side of the optician's shop B. When a /network connection/ menu is selected from the set menu shown in FIG. 4, a screen for designating the connection point is alternatively shown on the screen, therefore, by operating the movement switches 60b and 60c and so on, the eye examining unit 100B placed at the optician's shop B is designated as the connection point.

After the two eye examining units 100 and 100B are connected, the data of inquiry, objective value and the like are transferred and stored into the memory 33B of the controller 3B via the relay unit 5B located at the optician's shop B, and then the message that the connection has been completed is displayed on the screen of the displays 34 and 34B on each controller 3 and 3B. Accordingly, the examiner at the optician's shop B can find out that the connection has been completed. The examiner is also able to obtain the inquiry data of the examinee by selecting the /inquiry/ menu shown on the menu screen. Additional information of the inquiry can be confirmed by using the microphones 8 and 8B and the speakers 9 and 9B, which are connected to the both eye examining units.

Utilizing the screen of the display 34B as a screen for an examination, the examiner confirms the data of the objective value and the data of the previous spectacles value, and then starts the examination. An examination procedure, as one example, is carried out in the following order; first, a preliminary test including an unaided visual acuity test and a previous spectacled visual acuity test, and then a confirmation test of an objective visual acuity to check over the suitability of the obtained data of the objective value, a first R/G (red /green) test performed at the previous stage to an astigmatism test, an astigmatism axis detecting test, an astigmatism degree detecting test, a second R/G (red /green) test to obtain the maximum vision with preventing overcorrection, a binocular balance test, and finally, a subjective test to make adjustment for the obtained degree. An ophthalmic examination can be also carried out by applying an optometry program.

During these tests, questions to the examinee and the answers to the questions can be made through the microphones 8 and 8B and the speakers 9 and 9B. In the case of presenting a test target (chart) to the eye to be examined, if the target (chart) is selected by using the target (chart) switch group 61B on the controller 3B, then the signals concerning the target (chart) is transferred via the relay unit 5B, the modem 1B, the public communication network 18, the modem 1, and then the relay unit 5, so as to be inputted to the target (chart) presenting device 4. Accordingly, the selected test target (chart) is presented on the screen placed ahead of the examinee. Since the target (chart) being presented is shown in patterns also below the screen of the display 34B of the controller 3B at the examiner's site, the examiner can see the state of the target (chart) which is being presented (see FIG. 5). In the case of changing an optical system of the subjective refractive power measuring device 2, the measured value is inputted by operating the measurement mode switch of the switch group 63B and the dial switch 68B on the controller 3B, and the like. Signals concerning the refractive power from the controller 3B is transferred via the public communication network 18 and the like, and inputted to the subjective refractive power measuring device 2 placed in front of the eye of the examinee, and then the microcomputer circuit 20 changes the optical system based on the inputted signals. Information of the measurement is displayed on the screen of the display 34B on the controller 3B at the examiner's site (see FIG. 5).

As described above, the examiner at a separate location can remotely operate the controller 3B based on the information which is displayed on the display screen 34B, and the response from the examinee. In addition, these kinds of information of the optometry is also displayed on the display screen 34 placed at the optician's shop A and the measured data is stored in both of the memories 33 and 33B on the controllers 3 and 3B respectively.

After the examination is over, the examiner depresses a switch corespondents to the end of examination among the switches of function switch group 71B on the controller 3B. In response to the signal generated by this operation, the network connection is disconnected and the message displayed on the display screens 34 and 34B, which indicates the communication network is in connection, is turned off.

After confirming that the examination is over, the assistant at the optician's shop A depresses the print switch 66 to print out the respective measured results (It is also possible to make an arrangement for automatic printout responding to the signal of the completion of the examination). Thereby, the tested result can be also known at the site of the optician's shop A.

As described above, it is possible to remotely operate the examining devices placed at an optician's shop where a request is made without the constant presence of a skilled examiner, therefore, examinations at optician's shops can be flexibly dealt with. Besides, the numbers of skilled examiners and the training at optician's shops can be decreased. Further, if chain stores having numbers of brunch stores make their headquarters equipped with necessary devices, they can apply a system, in which an ophthalmic examination is ready to be performed at any time on demand.

In the above embodiment, the examiner is to perform an examination using the eye examining unit 100B having the same construction with the eye examining unit 100 at the examinee's site. However, if the apparatus includes means for operating the controller 3B and means for questioning and answering between the examiner and the examinee, it is possible to perform an examination at a separate location.

Further, the switch signals (except the necessary switch signals) transmitted from the controller 3 placed at the examinee's site can be made to be rejected, so as to prevent wrong operation of the controller 3 and malfunction of the devices placed at the examinee's site during the time the communication network is in connection.

Moreover, an improvement can be made if a TV camera for taking an image of the examinee's face is connected to the eye examining unit 100 and a monitor for projecting the image photographed by the TV camera is provided for the examiner's site at a separate location, so that the examiner is able to see the face and the expressions of the examinee while operating the examination, therefore, more appropriated prescriptions may be obtained. By placing TV cameras and monitors to the two different sites, the communication can be carried out more smoothly.

Figure 6:
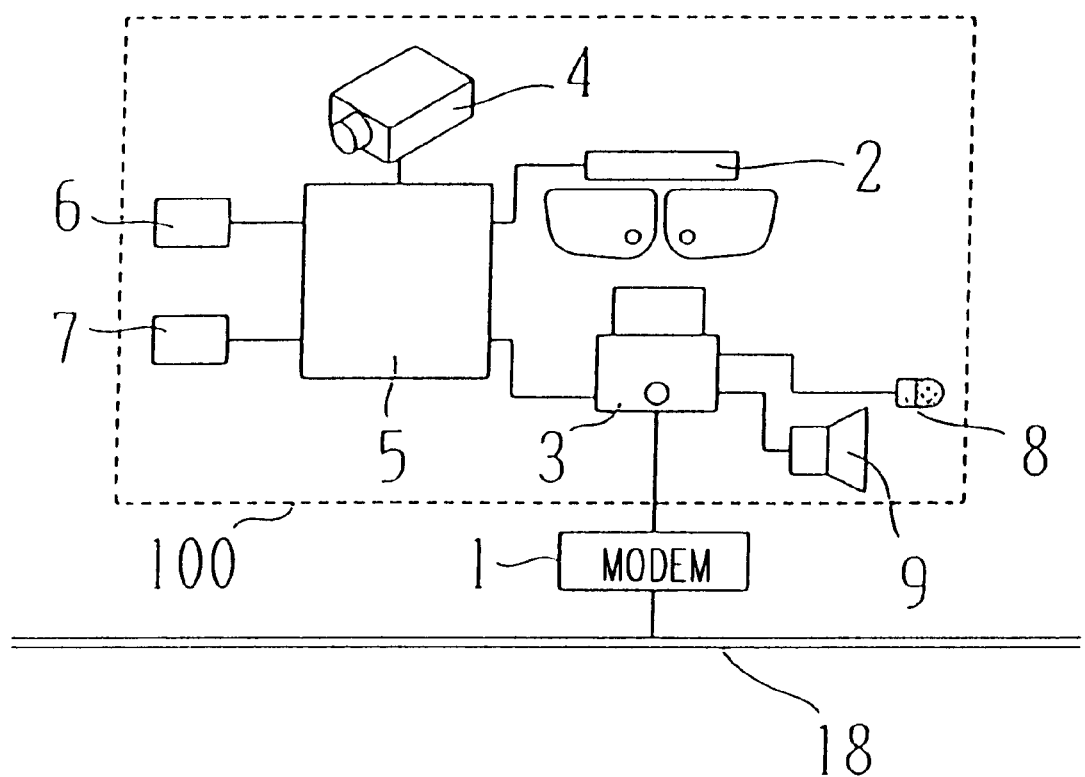
FIG. 6 is a view showing a modified form of connection between an eye examining unit and a modem.

In addition, as shown in the FIG. 6, relating to the connection of the eye examining unit 100 and the public communication network 18, the apparatus can be also configured as follows, the controller 3 and the public communication network 18 are directly connected via the modem 1. In that case, the microphone 8 and the speaker 9 are also connected to the controller 3.

In addition, according to the description in the above embodiment, the controller 3 is for an exclusive use of controlling each examining device. However, personal computers and display screens on public sale can be utilized as well.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is the claimed is:

1. A telecommunication system for examining an eye comprising:

plural eye examining units which include testing means for testing visual performance of an eye to be examined and operating means for operating said testing means, each of said units is connected via a communication network; and each of said eye examining units comprising:

sending means for sending the data obtained by said testing means to another eye examining unit;

receiving means for receiving the data sent from another eye examining unit; and instruction means for giving instructions to said testing means of another eye examining unit.

2. The telecommunication system according to claim 1, wherein said communication network is a public communication network.

3. The telecommunication system according to claim 1, wherein said testing means comprising at least one of the following devices:

a subjective refractive power measuring device for measuring a refractive power of the eye subjectively by placing a correcting optical system in front of the eye;

a target presenting device for presenting a target for a visual acuity test;

an objective refractive power measuring device for measuring the refractive power of the eye objectively by projecting a target for measurement onto a fundus, and then detecting the target image optically; and a lens meter for measuring the lens power of previous spectacles.

4. The telecommunication system according to claim 1, wherein said eye examining units comprising memory means for memorizing the visual performance data of the eye, which is obtained by said testing means.

5. The telecommunication system according to claim 1, wherein said eye examining units comprising display means for displaying various optometry information.

6. The telecommunication system according to claim 1, wherein said eye examining units comprising output means for outputting the visual performance data of the eye which is obtained by said testing means.

7. The telecommunication system according to claim 1, wherein each of said eye examining units comprising communication means which enables communication between an examinee and an examiner operating one of said eye examining units different from the one which is being used to examine the examinee.

8. The telecommunication system according to claim 7, wherein said communication means comprising a microphone and a speaker to transmit an examiner's intention.

9. An ophthalmic apparatus used for a telecommunication system comprising:

testing means for testing visual performance of an eye to be examined;

operating means for activating said testing means which is placed at a separate location than an examinee;

telecommunication means for connecting said operating means and said testing means via a communication network;

communication means which enables communication between an examiner operating said operating means and the examinee being examined with said testing means.

10. The ophthalmic apparatus according to claim 9, wherein said communication network is a public communication network.

11. The ophthalmic apparatus according to claim 9, wherein said testing means comprising at least either a target presenting device for presenting a target for a visual acuity test or a subjective refractive power measuring device for measuring a refractive power of the eye subjectively by placing a correcting optical system in front of the eye, whereby each of said devices being driven electrically by a signal from said operating means.

12. An ophthalmic apparatus used for a telecommunication system comprising:

testing means for testing visual performance of an eye to be examined;

a first operating means for activating said testing means, which is placed at the same location as an examinee;

a second operating means for activating said testing means, which is placed at a separate location than the examinee;

telecommunication means for connecting said second operating means and said testing means via a communication network; and communication means which enables communication between an examiner operating said second operating means and the examinee being examined with said testing means via said communication network.

13. The ophthalmic apparatus according to claim 12, wherein said communication network is a public communication network.

14. The ophthalmic apparatus according to claim 12, wherein said testing means comprising at least either a target presenting device for presenting a target for a visual acuity test or a subjective refractive power measuring device for measuring a refractive power of the eye subjectively by placing a correcting optical system in front of the eye, whereby each of said devices being driven electrically by a signal from said operating means.

* * * * *